US000001827H

United States Statutory Invention Registration [19]

[11] Reg. Number: H1,827

Cooper et al.

[45] Published: Jan. 4, 2000

[54] FIBROUS AND APERTURED, THREE-DIMENSIONAL MACROSCOPICALLY EXPANDED PLASTIC WEB

[76] Inventors: John T. Cooper, 7333 Tarragon Ct., West Chester, Ohio 45069; John J. Litchholt, 101 Hopping Ct., Harrison, Ohio 45030; Brian F. Gray, 1549 Riley Ave., Burlington, Ontario, Canada, L7M3E9; Michael J. Schettler, 41 Kipling Pl., Barrie, Ontario, Canada, L4N4W9; Gregory Ashton, 48 Burwell Crescent, Markham, Ontario, Canada, L3P6T8

[21] Appl. No.: 08/872,569

[22] Filed: Jun. 10, 1997

Related U.S. Application Data

[60] Continuation of application No. 08/485,197, Jun. 7, 1995, abandoned, which is a division of application No. 08/154,660, Nov. 18, 1993, abandoned.

[51] Int. Cl.[7] ..... B29C 65/00

[52] U.S. Cl. ..... 156/285

[58] Field of Search ..... 156/166, 167, 156/209, 252, 285; 428/137; 264/504, 517, 570, 571, 101, 154, 257

[56] References Cited

U.S. PATENT DOCUMENTS

| | | | |
|---|---|---|---|
| 3,043,738 | 7/1962 | Demeter et al. | 156/229 |
| 3,077,882 | 2/1963 | Trewella | 128/156 |
| 3,081,515 | 3/1963 | Griswold et al. | 28/78 |
| 3,165,432 | 1/1965 | Plaskett | 156/244 |
| 3,190,781 | 6/1965 | Metz, Jr. | 156/244 |
| 3,331,728 | 7/1967 | Lane | 161/112 |
| 3,421,964 | 1/1969 | Arbit | 156/244 |
| 3,523,149 | 8/1970 | Hartmann | 264/90 |
| 3,878,014 | 4/1975 | Melead | 156/167 |
| 3,881,488 | 5/1975 | Delanty et al. | 128/287 |
| 3,911,186 | 10/1975 | Trotman | 428/137 |
| 3,917,501 | 11/1975 | Ferrucci et al. | 156/279 |

(List continued on next page.)

FOREIGN PATENT DOCUMENTS

| | | | |
|---|---|---|---|
| 0 018684 | 11/1980 | European Pat. Off. | A41B 13/02 |
| 0 040 084 | 11/1981 | European Pat. Off. | A61F 13/00 |
| 0 295 694 | 12/1988 | European Pat. Off. | B32B 27/12 |
| 0 409 535 A1 | 1/1991 | European Pat. Off. | D04H 11/08 |
| 0 545 423 A1 | 6/1993 | European Pat. Off. | A61F 13/15 |
| 57-191022 | 11/1982 | Japan | B29D 07/14 |
| 2-193663 | 7/1990 | Japan | A61F 13/15 |
| 4-152945 | 5/1992 | Japan | 604/378 |
| 5-137752 | 6/1993 | Japan | 604/378 |
| 932757 | 2/1965 | United Kingdom . | |
| WO 93/09741 | 5/1993 | WIPO | A61F 13/15 |
| WO 93/12749 | 7/1993 | WIPO | A61F 13/15 |
| WO 93/22995 | 11/1993 | WIPO | A61F 13/15 |
| 9424354 | 11/1994 | WIPO . | |

*Primary Examiner*—Charles T. Jordan
*Assistant Examiner*—Meena Chelliah

[57] ABSTRACT

A fluid pervious web suitable for use as a topsheet on an absorbent article is disclosed. The topsheet includes a fibrous and apertured, three-dimensional, macroscopically expanded, plastic web. The fibrous and apertured, three-dimensional, macroscopically expanded, plastic web permits bodily fluids to penetrate while providing an improved, less plastic-like feel and visual aesthetics.

1 Claim, 8 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS

| | | | |
|---|---|---|---|
| 3,929,135 | 12/1975 | Thompson | 128/287 |
| 3,945,386 | 3/1976 | Anczurowski et al. | 128/287 |
| 3,965,906 | 6/1976 | Karami | 128/287 |
| 3,967,623 | 7/1976 | Butterworth et al. | 128/287 |
| 3,987,792 | 10/1976 | Hernandez et al. | 128/284 |
| 3,994,299 | 11/1976 | Karami | 128/287 |
| 4,077,410 | 3/1978 | Butterworth et al. | 128/287 |
| 4,323,069 | 4/1982 | Ahr et al. | 128/287 |
| 4,342,314 | 8/1982 | Radel et al. | 128/287 |
| 4,463,045 | 7/1984 | Ahr et al. | 604/370 |
| 4,609,518 | 9/1986 | Curro et al. | 264/504 |
| 4,619,724 | 10/1986 | Chatow | 156/72 |
| 4,622,036 | 11/1986 | Goodrum | 604/367 |
| 4,695,422 | 9/1987 | Curro et al. | 264/504 |
| 4,726,976 | 2/1988 | Karami et al. | 428/137 |
| 4,741,877 | 5/1988 | Mullane, Jr. | 264/504 |
| 4,747,991 | 5/1988 | Bishop | 264/504 |
| 4,781,962 | 11/1988 | Zamarripa et al. | 428/138 |
| 4,797,246 | 1/1989 | Reinke et al. | 264/504 |
| 4,878,825 | 11/1989 | Mullane, Jr. | 425/290 |
| 4,985,023 | 1/1991 | Blank et al. | 604/360 |
| 4,995,930 | 2/1991 | Merz et al. | 156/209 |
| 5,019,062 | 5/1991 | Ryan et al. | 604/359 |
| 5,171,238 | 12/1992 | Kajander | 604/383 |
| 5,173,351 | 12/1992 | Ruppel et al. | 428/1.74 |
| 5,282,915 | 2/1994 | Westlake, Jr. | 156/243 |
| 5,368,909 | 11/1994 | Langdon et al. | 428/137 |
| 5,368,910 | 11/1994 | Langdon | 428/137 |
| 5,383,870 | 1/1995 | Takai et al. | 604/370 |
| 5,387,209 | 2/1995 | Yamamoto et al. | 604/366 |
| 5,514,308 | 5/1996 | Cohen et al. | 264/442 |

FIBROUS AND APERTURED, THREE-DIMENSIONAL MACROSCOPICALLY EXPANDED PLASTIC WEB

CROSS-REFERENCE TO RELATED APPLICATION

This application is a continuation of 08/485,197 filed on Jun. 7, 1995 abandoned on Jun. 11, 1997, which is a division of application Ser. No. 08/154,660 filed on Nov. 18, 1993, abandoned on Nov. 19, 1996.

FIELD OF THE INVENTION

The present invention relates to absorbent articles such as sanitary napkins, pantiliners, disposal diapers, incontinent articles, and the like, and more particularly, the present invention relates to absorbent articles having a fibrous and apertured, three-dimensional, macroscopically expanded, plastic topsheet.

BACKGROUND OF THE INVENTION

All manner and variety of absorbent articles configured for the absorption of bodily fluids are, of course, well known. Current types of absorbent articles include sanitary napkin, pantiliners, disposable diapers, and incontinent articles.

Macroscopically expanded, three-dimensional, apertured, films have been used as topsheets on such absorbent articles. As used herein, the term "macroscopically expanded", when used to describe three-dimensional, plastic webs, ribbons and films, refers to webs, ribbons and films, which have been caused to conform to the surface of a three-dimensional forming structure so that both surfces thereof exhibit the threedimensional pattern of the forming structure, the pattern being readily visible to the naked eye when the perpndicular distance between the viewer's eye and the plane of the web is about 12 inches.

One macroscopically expanded, three-dimensional, apertured plastic web which is particularly well suited to transferring fluid deposited on one surface thereof to its opposite surface and thereafter isolating the transferred fluid from the wearer's skin is disclosed in commonly assigned U.S. Pat. No. 3,929,135 issued to Thompson on Dec. 30, 1975, and hereby incorporated herein by reference. Thompson describes a macroscopically expanded, three-dimensional, topsheet comprised of liquid impermeable material, but provided with a pattern of tapered capillaries, the capilaries have a base opening in the plane of the topsheet contacting the wearer's body and an apex opening remote from the base opening of the topsheet, the apex opening being in intimate contact with the absorbent pad utilized in the disposable absorbent article. The Thompson topsheet allows for the free transfer of fluid from the wearer's body into the absorbent element of the device while inhibiting the reverse flow of these fluids. This provides a relatively much dryer surface in contact with the user than had previously been obtainable.

Another macroscopically expanded, three-dimensional, apertured plastic web well suited for use as a topsheet on absorbent articles such as sanitary napkins is disclosed in commonly assigned U.S. Pat. No. 4,342,314 issued to Radel et al. on Aug. 3, 1982, said patent being hereby incorporated herein by reference. The macroscopically expanded, three-dimensional plastic web disclosed in the Radel et al. patent exhibits a fiber-like appearance and tactile impression which has been favorably received by c;nsumers when used as a wearer contacting surface.

While macroscopically expanded, three-dimensional, apertured plastic webs have achieved widespread commercial success when employed as topsheets on absorbent articles, some users are very reluctant to place a topsheet which they readily perceive as plastic in contact with their skin.

Accordingly, it is therefore an object of the present invention to provide a topsheet for an absorbent article having fluid handling characteristics comparable to those found in macroscopically expanded, three-dimensional apertured plastic topsheets and an improved softer, less plastic-like feel.

SUMMARY OF THE INVENTION

The present invention relates to absorbent articles such as diapers, incontinent articles, sanitary napkins, and the like. More particularly, this invention relates to absorbent articles having a composite fibrous and macroscopically expanded, three-dimensional, apertured plastic film topsheet. The resilient, three-dimensional, macroscopically expanded, fluid pervious plastic web has a first surfic and a second surface located in planes remote from one another. A plurality of capillaries extend from the first surface to the second surface of the plastic web. The capillaries are defined by a plurality of sidewall portions interconnected to one another intermediate the first and second surfaces and terminate in the second surface. A plurality of fibers are secured to the first surface of the fluid pervious plastic web. The fibers extend into the capillaries of the fluid pervious plastic web and are secured to the sidewall portions.

The present invention also provides a process for forming a fibrous and apertured, three-dimensional, macroscopically expanded, plastic web. A polymeric film is extruded onto a forming structure. The forming structure exhibits a macroscopic, three-dimensional, cross-section defined by a multiplicity of macroscopic apertures which place the opposed surface of the forming structure in fluid communication with one another. A plurality of fibers are deposited on the film while the film is supported by the forming structure to form a composite web. A pneumatic pressure differential is applied to the composite web of film and fibers to cause the composite web to be urged into substantial conformance with the macroscopic, three-dimensional, cross-section of the forming structure forming a three-dimensional, macroscopically expanded, web having a plurality of capillaries extending from the first surface to said second surface. The capillaries are defined by a plurality of sidewall portions interconnected to one another intermediate the first and second surfaces and which terminate in the second surface. The pneumatic pressure causes the fibers to be pulled against the first surface of the formed web and into the capillaries of the formed web. The fibers are secured to the first surface and the sidewall portions of said formed web forming a fibrous and apertured, three-dimensional, macroscopically expanded web.

BRIEF DESCRIPTION OF THE DRAWINGS

While the specification concludes with claims particularly pointing out and distinctly claiming the present invention, it is believed that the present invention will be better understood from the following description in conjunction with the accompanying drawings in which:

DETAILED DESCRIPTION OF THE PRESENT INVENTION

Figure 1:
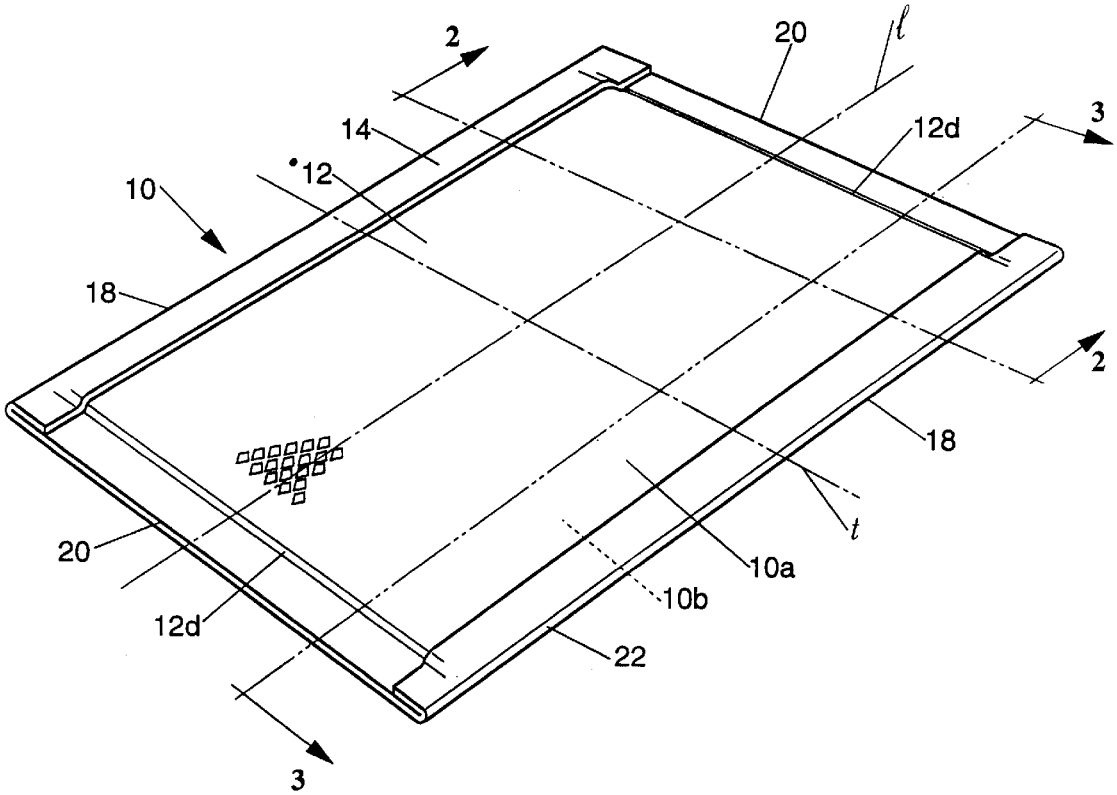
FIG. 1 is a simplified perspective view of an absorbent article of the present invention.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include diapers, incontinent articles, sanitary napkins, pantiliners, and other articles used to absorb body exudates. The term "disposable" is used herein to describe absorbent articles which are not intended to be laundered or otherwise restored or reused as an absorbent article, i.e., they are intended to be discard after a single use, and, preferably to be recycled, composted or otherwise disposed of in an environmentally compatible manner.

The term "diaper" refers to a garment generally worn by infants and incontinent persons which is worn about the lower torso of the wearer. Suitable diapers that can be provided with the topsheet described herein are disclosed in U.S. Pat. No. Re. 26,152, issued to Duncan, et al. on Jan. 31, 1967; U.S. Pat. No. 3,860,003 issued to Buell on Jan. 14, 1975; U.S. Pat. No. 4,610,678 issued to Weisman, et al. on Sep. 9, 1986, U.S. Pat. No. 4,673,402 issued to Weisman, et al. on Jun. 16, 1987; U.S. Pat. No. 4,695,278 issued to Lawson on Sep. 22, 1987; U.S. Pat. No. 4,704,115 issued to Buell on Nov. 3, 1987; U.S. Pat. No. 4,834,735 issued to Alemany et al. on May 30, 1989; U.S. Pat. No. 4,888,231 issued to Angstadt on Dec. 19, 1989; and U.S. Pat. No. 4,909,803 issued to Aziz, et al. on Mar. 20, 1990; each of which is incorporated herein by reference.

The term "incontinent article" refers to pads, undergarments (pads held in place by a suspension system of some type, such as a belt, or the like), inserts for absorbent articles, capacity boosters for absorbent articles, briefs, bed pads, and the like, regardless of whether they are worn by adults or other incontinent persons. Suitable incontinent articles that can be provided with the topsheet described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat No. 4,704,115; U.S. Pat. No. 4,909,802 issued to Ahr, et al.; and U.S. Pat. No. 4,964,860 issued to Gipson, et al. on Oct. 23, 1990; each of which is incorporated herein by reference.

The term "sanitary napkin" refers to an article which is worn by females adjacent to the pudendal region that is intended to absorb and contain various exudates which are discharged from the body (e.g., blood, menses and urine). Suitable sanitary napkins that can be provided with the topsheet described herein are disclosed in U.S. Pat. No. 4,285,343, issued to McNair on Aug. 25, 1981; U.S Pat. Nos. 4,589,876 and 4,687,478 issued to Van Tilburg on May 20, 1986 and Aug. 18, 1987 respectively; U.S Pat. Nos. 4,917,697 and 5,007,906 issued to Osborn, et al. on Apr. 17, 1990 and Apr. 16, 1991, respectively; and U.S. Pat. Nos. 4,950,264 and 5,009,653 issued to Osborn on Aug. 21, 1990 and Apr. 23, 1991, respectively; each of which is incorporated herein by reference.

The term "pantiliner" refers to absorbent articles that are less bulky than sanitary napkins which are generally worn by women between their menstrual periods. Suitable pantiliners that can be provided with the topsheet descnibed herein are disclosed in U.S. Pat. No. 4,738,676 issued to Osborn on Apr. 19, 1988.

Figure 2:
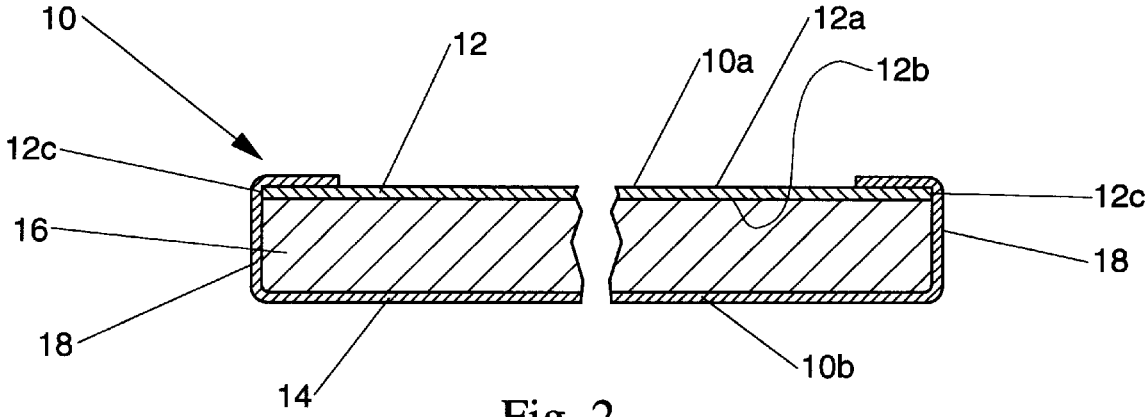
FIG. 2 is a cross-sectional view taken along section line 2—2 of FIG. 1.
Figure 3:
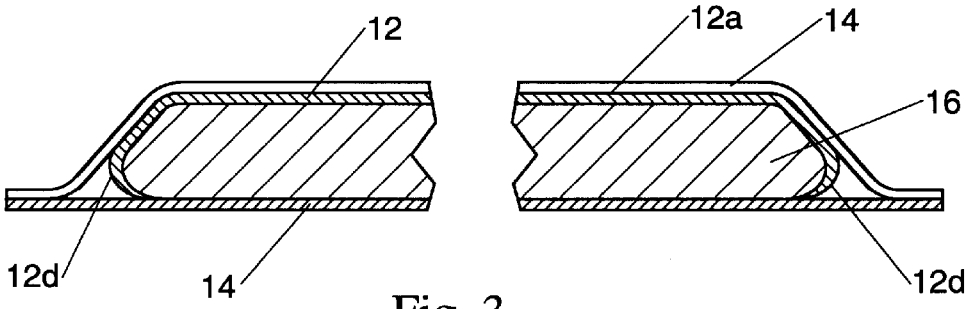
FIG. 3 is a cross-sectional view taken along section line 3—3 of FIG. 1.

FIG. 1 shows a simplified absorbent article 10 that could represent a diaper prior to its being placed on a wearer. It should be understood, however, that the present invention is not limited to the particular type or configuration of absorbent article shown in the drawings. As shown in FIGS. 2 and 3, such an absorbent article 10 basically comprises a topsheet 12, a backsheet 14, and an absorbent core 16.

The absorbent article 10 has two surfaces, a body-contacting surface (or "body surface") 10*a* and a garment surface 10*b*. The body surface 10*a* is intended to be worn adjacent to the body of the wearer. The garment surfa lOb of the absorbent article 10 (shown in FIG. 2) is on the opposite side and is intended to be placed adjacent to the wearer's undergarments or clothing when the absorbent article 10 is worn.

The absorbent article 10 has two centerlines, a longitudinal centerline 1 and a transverse centerline t. The term "longitudinal", as used herein, refers to a line, axis or direction in the plane of the absorbent article 10 that is generally aligned with (e.g., approximately parallel to) a vertical plane which bisects a standing wearer into left and right body halves when the absorbent article 10 is worn. The terms "transverse" or "lateral" as used herein, are interchangeable, and refer to a line, axis or direction which lies within the plane of the absorbent article 10 that is general perpendicular to the longitudinal direction. FIG. 1 shows that the absorbent article 10 has two spaced apart longitudinal edges 18 and two spaced apart transverse or end edges (or "ends") 20, which together form the periphery 22 of the absorbent article 10.

The topsheet 12 is compliant, soft-feeling and non-irritating to the wearer's skin. Further, topsheet 12 is liquid permeable, permitting liquids to readily penetrate through its thickness. The topsheet 12 has a body-facing side or face 12*a* and a garment-facing side or face 12*b*, two longitudinal or side edges 12*c* and two end edges 12*d*. (A similar numbering system will be used for the other components of the diaper 10. That is, the side of the component facing the wearer's body will be designated by the number of the component and a reference letter "a", the side facing the wearer's undergarments by the number of the component and the letter "b", and the side and end edges by the number of the component and the reference letters "c" and "d" respectively.)

Figure 4:
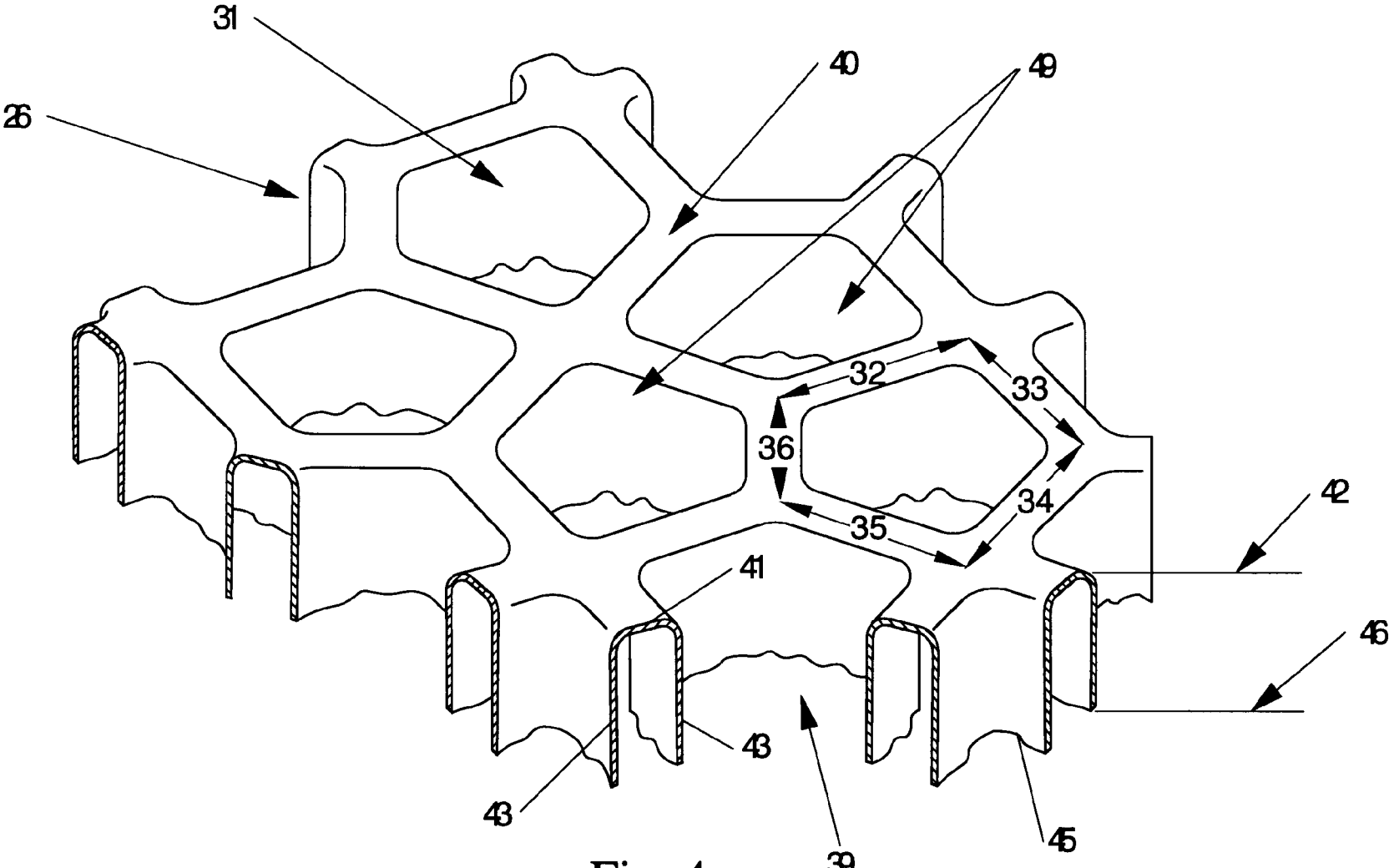
Fig. 4 (Prior Art)
FIG. 4 is an enlarged, partially segmented, perspective illustration of a prior art plastic web of the type generally enclosed in commonly assigned U.S. Pat. No. 4,342,314.

FIG. 4 is an enlarged, partially segmented, perspective illustration of a prior art macroscopically expanded, three-dimensional, fiber-like, apertured, plastic film 26 which has been found highly suitable for use as a topsheet in disposal absorbent articles. Prior art plastic film 26 is generally in accordance with the teachings of commonly assigned U.S. Pat. No. 4,342,314 issued to Radel, et al. on Aug. 3, 1982, and is hereby incorporated herein by reference. The plastic film 26 exhibits a multiplicity of apertures, e.g., apertures 31, which are formed by a multiplicity of intersecting fiber-like elements, e.g., elements 32, 33, 34, 35 and 36 interconnected to one another in the first surfiace 40 of the web. Each fiber-like element comprises a base portion, e.g., base portion 41 located in plane 42. Each base portion has a sidewall portion, e.g., sidewall portions 43, attached to each edge thereof. The sidewall portions extend generally in the direction of a second surface 45 of the web. The intersecting sidewall portions of the fiber-like elements are interconnected to one another intermediate the first and second surfaces of the web, and tenminate substantially concurrently with one another in the plane 46 of the second surface to form apertures 39 in the second surface 45 of the web. The capillaries 49 formed by the interconnected sidewall portions allows for free transfer of fluid from the first surce of the web directly to the second surface of the web without lateral transmission of the fluid between the adjacent capillaries.

The apertured plastic film 26 is manufactured from a liquid impervious, preferably thermoplastic material. The thermoplastic material for use in the manufacture of the apertured plastic film 26 is selected from a group generally consisting of polyethylene, polypropylene, polyvinyl chloride, starch base resins, polyvinyl alcohol, polyurethanes, polycaprolactone cellulose esters and blends thereof.

Examples of other macroscopically expanded, three-dimensional, apertured, plastic webs are disclosed in U.S. Pat. No. 3,939,135 issued to Thompson on Dec. 30, 1975; U.S. Pat. No. 4,324,426, issued to Mullane, et al. on Apr. 13, 1982; and U.S. Pat. No. 4,463,045, issued to Ahr, et al on Jul. 31, 1984; each of said patents being hereby incorporated herein by reference.

Figure 6:
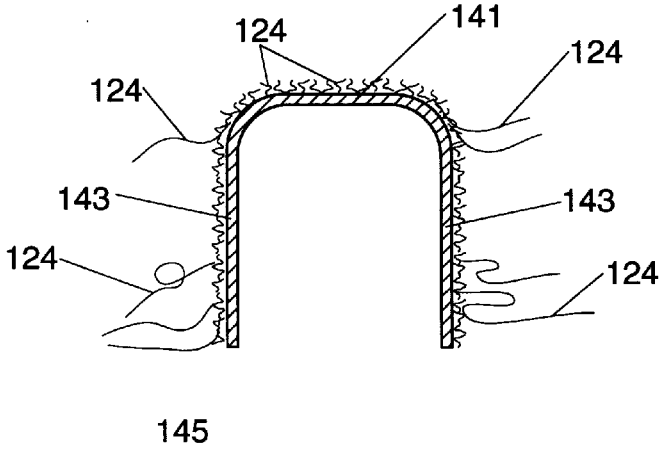
FIG. 6 is an enlarged, cross-sectional view of a fiber-like element of the fibrous and apertured, plastic web of the present invention taken along section line 6—6 of FIG. 5.
Figure 5:
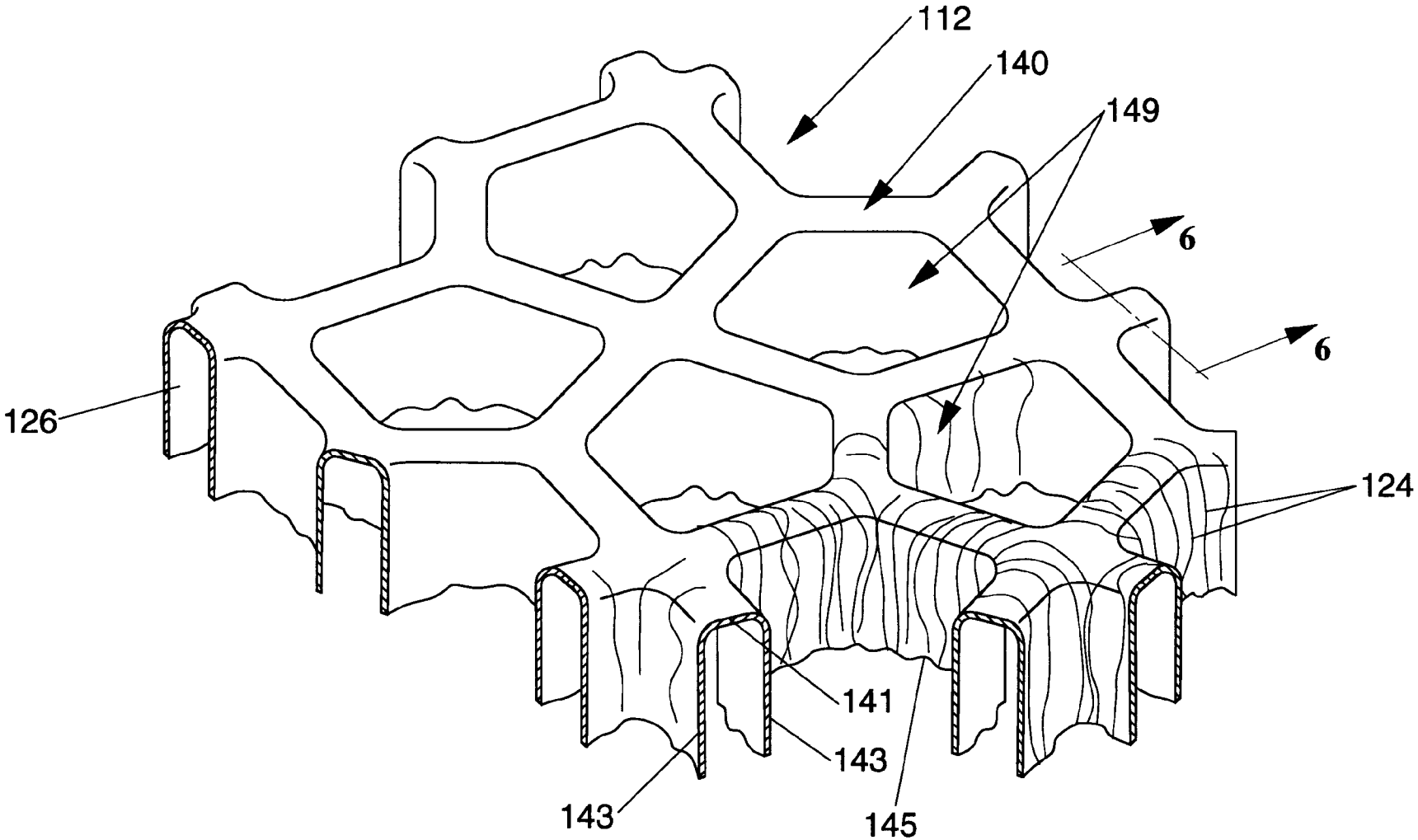
FIG. 5 is an enlarged, partially segmented, perspective illustration of a preferred embodiment of the fibrous and apertured, plastic web of the present invention.

FIG. 5 is an enlarged, partially segmented, perspective illustration of a particularly preferred embodiment of a fibrous and apertured, plastic web 112. Fibrous and apertured plastic web 112 is particularly well suited for use as a topsheet, e.g., topsheet 12 illustrated in FIG. 1, on an absorbent article, such as a diaper or sanitary napkin. Web 112 comprises a plurality of fibers 124 secured to a macroscopically expanded, three-dimensional, :;nertured, plastic web 126. Apertured plastic web 126 is generally in accordance with the teachings of commonly assigned U.S. Pat. No. 4,342,314 issued to Radel et al. Referring now to FIG. 6, the fibers 124 are secured to the apertured plastic web 126 along the first surface 140 and extend substantially into the capillaries 149 where a substantial portion of the fibers 124 are secured to the sidewall portions 143 of the apertured plastic film 126. Despite the presence of fibers 124 the appearance of web 112, is generally similar to that of prior art web 26 illustrated in FIG. 4, that is, the pentagonal shape of capillaries 49 of web 26 is similar to the pentagonal shape of capillaries 149 of web 112.

By securing the fibers 124 to both the first surface 140 and the sidewall portions 143 of the apertured plastic web 126, a substantial portion of the fibers 124 do not span the capillaries 149, where the fibers would possibly hinder the transfer of bodily fluids from the first surface 140 to the second surface 145 of the web. By leaving the capillaries substantially open and free of fibers, the fibrous and apertured, composite web 112 is able to handle heavy or viscous fluids such as rumy BM, when the composite web is employed as a topsheet on a disposable diaper. Some fibers 124 may span across the capillaries 149, but they will not substantially hinder the transmission of bodily fluids from the first surface 140 to the second surface 145 of the web.

Due to the securement of the fibers 124 to the first surface 140 and the sidewall portions 143 of the apertured plastic web 126, the composite web 112 has an open area approaching that of apertured plastic web 126. Therefore, fluid deposited on the first surface 140 is transmitted from the first or wearer contacting surface to the second or pad contacting surface 145 of the composite web 112.

The addition of the fibers 124 to the first or wearer contacting surface of the apertured plastic web 126 provides a textured surface which when utilized as a topsheet on an absorbent article is in contact with the wearer's skin. The tactile perception of the web 112 is similar to that of a fibrous nonwoven web. The addition of the fibers to the wearer contacting surface of the apertured plastic film 126 reduces the plastic feel associated with such films which some users resist placing in contact with their skin.

The addition of the fibers 124 to the wearer contacting surface of the apertured plastic film 126 also provides the web 112 with a visual distinction from the plastic web 126. That is, the fibers provide a roughness or an irregularity such that light incident upon the visible surface of the web is substantially diffused into a multiplicity of directions rather than being speculary reflected, thereby providing a non-glossy visible surface which reduces the wearer's perception that the web is comprised of plastic.

In one preferred embodiment, the fibers 124 may be in the form of a nonwoven fabric or web. The nonwoven fabric may be manufactured from a wide range of material such as natural fibers (e.g., wood, or cotton fiber), synthetic fibers (e.g., polyester, polypropylene) or a combination thereof. The nonwoven fabric is preferably made from fibers selected from a group consisting of polypropylene, polyester, polyethylene polyvinyl alcohol, starch base resins, polyurethanes, cellulose and cellulose esters.

There are a number of manufacturing techniques which may be utilized to manufacture the nonwoven fabric. For example, nonwoven fabric may be resin-bonded, needle punched, spunbonded, carded, the latter including, thermally bonded, air-thru bonded, and spunlaced fabrics. A preferred nonwoven fabric is a thermally bonded polypropylene fabric.

The nonwoven fabric preferably has a relatively low basis weight ranging from about 1.0g/sq.m. to about 22 g/sq.m. For one embodiment, the nonwoven fabric has a basis weight range of from about 15 to about 17 grams per square yard (about 18 to about 20 g/sq.m.) aand a caliper of from about 3 to about 5 mils (about 0.76 to about 0.12 mm.) when measured under a load of about 200 pascals. Such a nonwoven fabric is further characterized by a maximum wet or dry tensile strength of less than about 600 grams per centimeter in the longitudinal or machine direction and less than about 150 grams per centimeter in the cross machine direction.

In another preferred embodiment, the nonwoven fabric has a lighter weight of from about 8 g/sq.m. to about 10 g/sq.m. Such lighter nonwoven fabrics are highly preferred. They are preferred because they can be used (with a lightweight film) to form a composite fibrous and apertured, plastic web 112 that is sufficiently thin and lightweight that it behaves as a single sheet of material. This provides the advantages of being more flexible and requiring the use of smaller amounts of raw materials.

In another preferred embodiment, the fibers 124 may be meltblown onto the plastic web 126. Preferably, the meltblown fibers 124 are deposited on the plastic web in a range of basis weights up to about 22 g/sq.m. and most preferably in a range of basis weights from about 2.0 g/sq.m. to about 5.0 g/sq.m. The meltblown fibers may be selected from a wide range of materials selected from the group consisting of polypropylene, polyester, polyethylene polyvinyl alcohol, starch base resins, polyurethanes, cellulose and cellulose esters. A detailed description of this particular method of securing the fibers 124 to the plastic web 126 is described in greater detail below.

Figure 7:
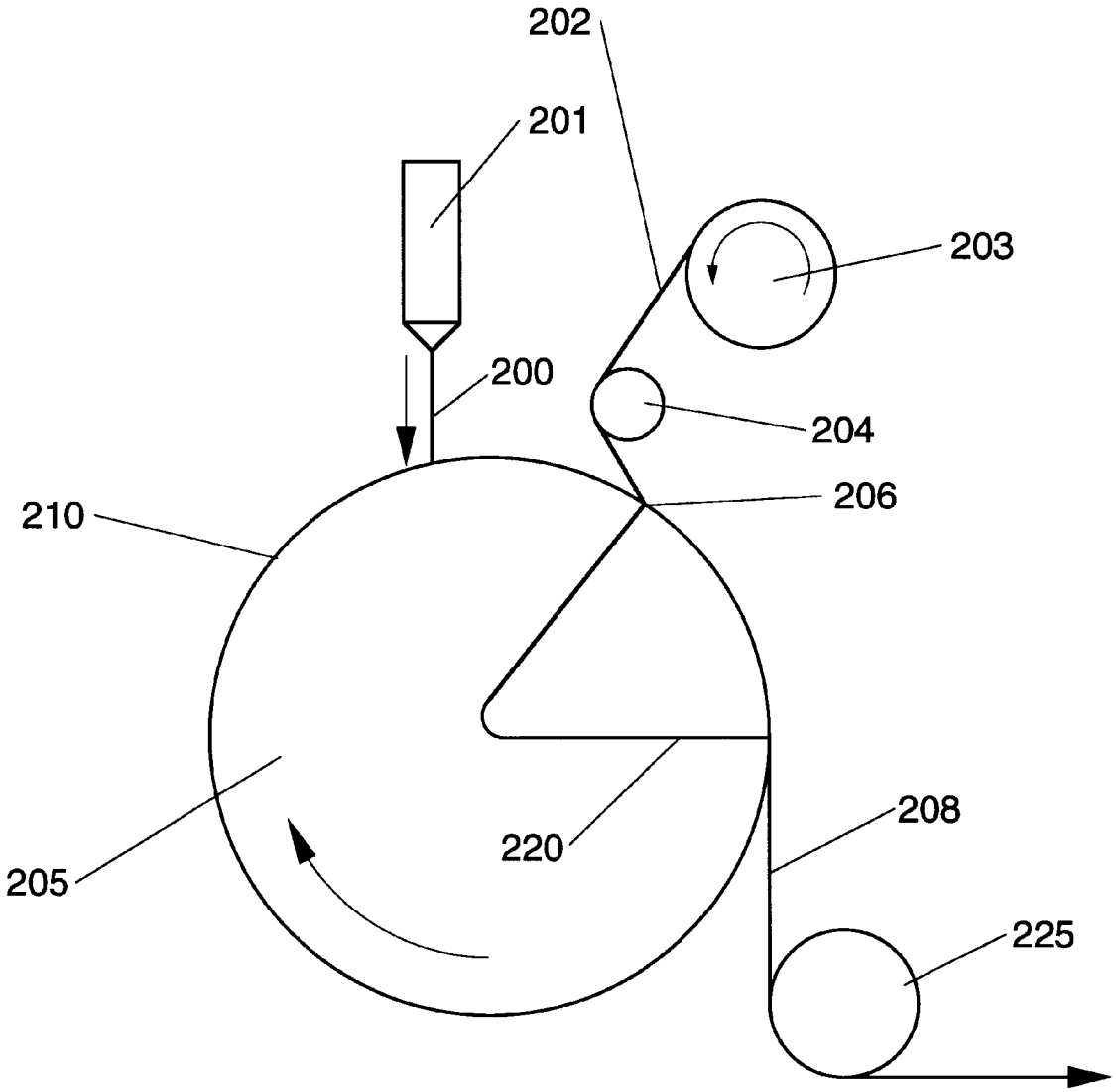
FIG. 7 is a simplified schematic representation of a process for making the fibrous and apertured, plastic web of the present invention.

A suitable process of preparing the fibrous and apertured, plastic web 112 of the present invention is shown in FIG. 7. In the embodiment shown in FIG. 7, a web of molten resin 200 is extruded from a conventional extruder 201 onto the surface of a forming drum 205 about which a forming structure 210 rotates. A web of nonwoven fabric 202 is fed from a supply roll 203 over nip roll 204 onto the web of molten resin 200 located on forming structure 210. The web of nonwoven fabric 202 adheres to the semi-molten resin forming a composite web 206. The forming drum 205 preferably includes an internally located vacuum chamber 220 which is preferably stationary relative to the moving forming structure 210. As the composite web 206 of semi-molten resin 200 and nonwoven fabric 202 passes across vacuum chamber 220 a pneumatic pressure is applied to the composite web to cause the composite web to be urged into substantial conformance with the forming structure 210.

Figure 8:
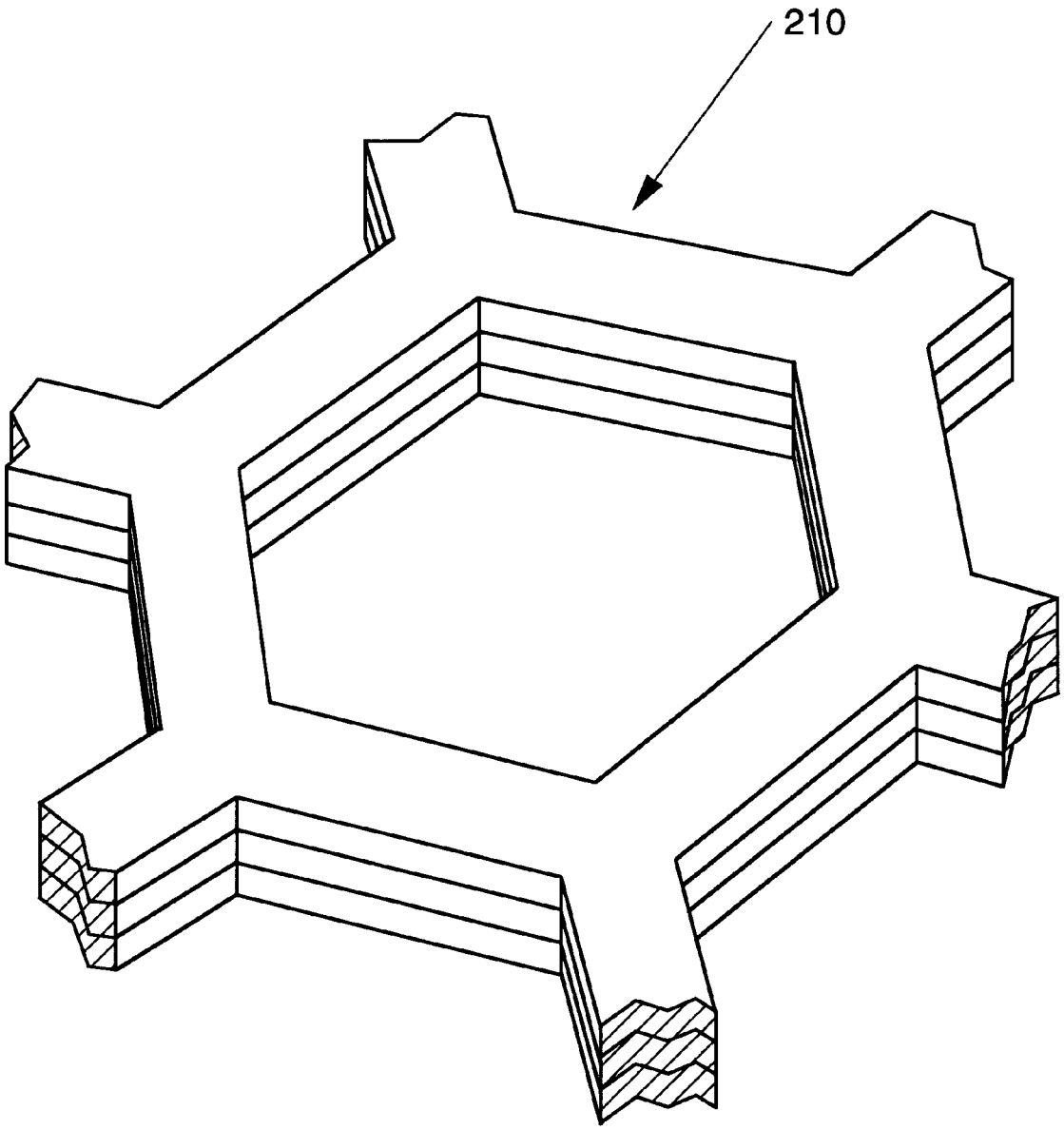
FIG. 8 is a greatly enlarged fragmentary view of the forming structure utilized to support the fibrous and apertured, plastic web in accordance with the process illustrated in FIG. 7.

The macroscopic cross-section of forming structure 210 is visible in the greatly enlarged fragmentary perspective illustration of FIG. 8. Methods of constructing a suitable three-dimensional tubular forming member similar to that illustrated in FIG. 8 are disclosed in commonly assigned U.S. Pat. No. 4,508,256 issued to Radel et al. on Apr. 2, 1985 and in commonly assigned U.S. Pat. No. 4,509,908 issued to Mullane, Jr. on Apr. 9, 1985, said patents being hereby incorporated herein by reference.

As the composite web 206 of semi-molten resin 200 and nonwoven fabric 202 conforms with the macroscopic cross-section of forming structure 210 a fibrous and three-dimensional, macroscopically expanded, apertured web is created similar to web 112 illustrated in FIG. 5. The web has a first surface and a second surface located in planes remote from one another. The formed web includes a plurality of capillaries which extend from the first surface to the second surface. The capillaries are defined by a plurality of sidewall portions interconnected to one another intermediate the first and second surfaces and which terminate in the second surface of the web.

The pressure of vacuum chamber 220 causes the nonwoven fabric to be pulled against the first surface of the plastic web and down into the capillaries of the plastic web. The pressure applied by the vacuum chamber 220 also helps to bond or secure the nonwoven fabric to the base portions and the sidewall portions of the first surface of the plastic web.

The composite web 208 is preferably treated with an effective amount of surface active agent or surfactant. The surfactant provides the nonwoven fabric's surface with greater polararizability than it would have without the surfactant being added. Higher surface polarity yields higher wet ability. Suitable surfactants include a product known commercially ATNER645 manufactured by ICIS Specialty Ch. The nonwoven fabric may be treated with a surfactant prior to or during the time it is manufactured. For example, it may be treated after it is unwound from feedroll 203. The surfactant may be applied by any know technique, such as spraying, padding, or by the use of transferals. The surfactant can alternatively (or additionally) be incorporated into the nonwoven fabric such as between or within the fibers of the nonwoven fabric. Preferably, the nonwoven is treated with a surfactant prior to the time it is supplied in the present process.

After the nonwoven fabric and apertured plastic film have been formed into composite web 208, composite web 208 is removed from forming drum 210 by way of nip roll 225. The composite web 208 may be fed to a rewind station for temporary storage or may be utilized without further processing as a topsheet in an absorbent article.

Figure 9:
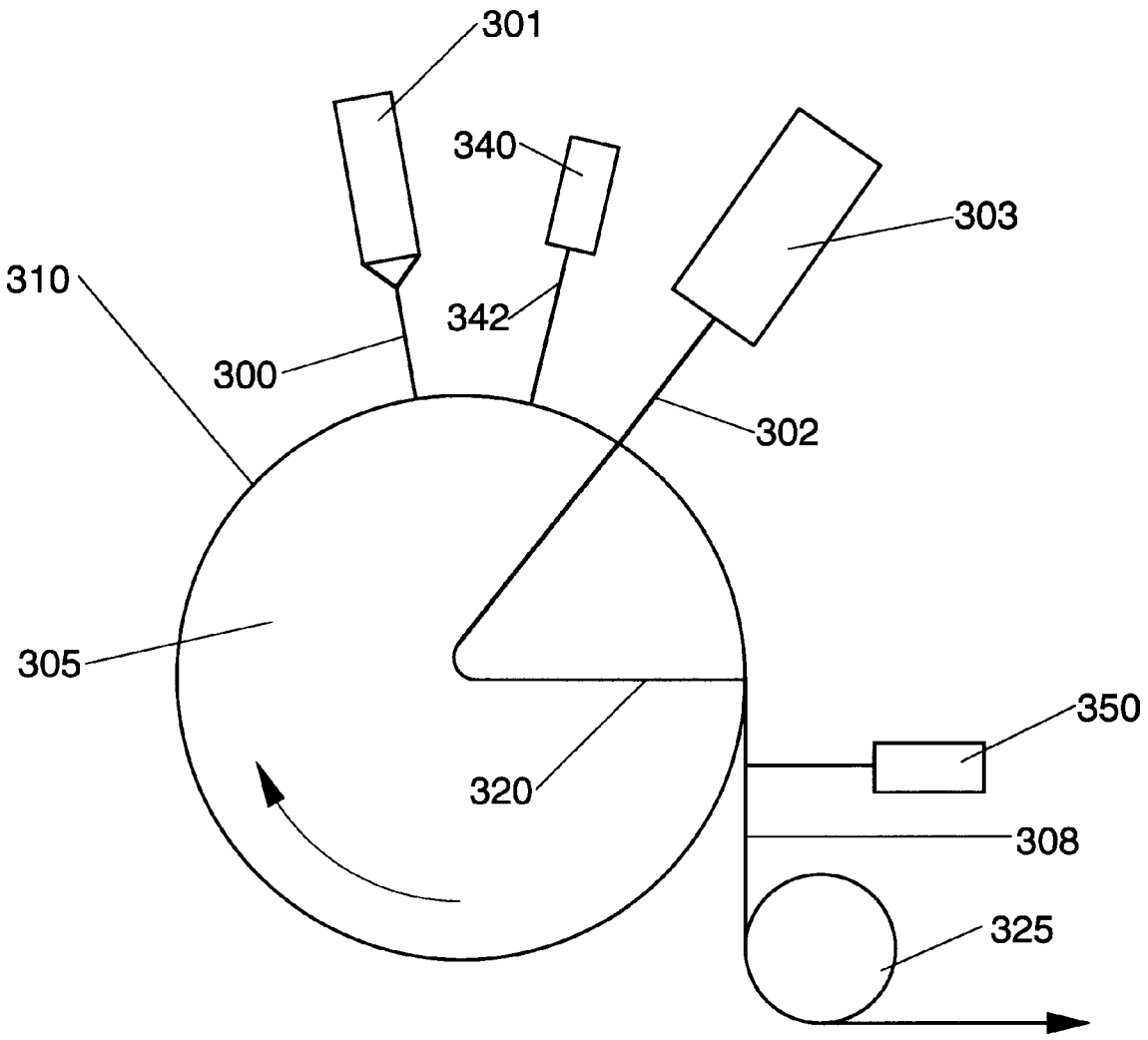
FIG. 9 is a simplified schematic representation of an alternative process for making the fibrous and apertured, plastic web of the present invention.

Another suitable process for preparing the topsheet 112 is shown in FIG. 9. In the embodiment shown in FIG. 9, a web of molten resin 300 is extruded from a conventional extruder 301 onto the surface of a forming drum 305 about which a forming structure 310 rotates. A stream of meltblown fibers 302 is blown from die 303 onto the web of molten resin 300 which is supported by forming structure 310. The forming drum 305 preferably includes an internally located vacuum chamber 320 which is preferably stationary relative to the moving forming structure 310. As the molten resin 300 and the meltblown fibers 302 pass across vacuum chamber 320 a pneumatic pressure is applied to the molten resin and the meltblown fibers to cause the resin along with the fibers to be urged into substantial conformance with the forming structure 310. The forming structure 310 is similar to forming structure 110 illustrated in FIG. 7.

In the embodiment of FIG. 9, a non-water soluble adhesive 342 may be added from applicator 340 onto molten resin 300 prior to the addition of meltblown fibers 302. The adhesive 342 helps ensure the attachment of meltblown fibers 302 to molten resin 300.

To create a topsheet similar to that illustrated in FIG. 5, where the nonwoven layer does not span across or block the capillaries of the apertured plastic film, the nonwoven or fibrous matter must be able to conform with the general shape of the macroscopically expanded, three-dimensional forming structure. To permit the nonwoven or fibrous matter to conform with the shape of the forming structure it must not be so dense or tightly bonded such that the individual fibers are not permitted to be pulled down into the capillaries of the apertured plastic film where they are secured with the sidewall portions of the apertured plastic web.

In another embodiment, the stream of meltblown fibers may be applied to a molten resin after the resin has been formed into a macroscopically expanded, three-dimensional, apertured plastic web, simllar to that illustrated in FIG. 4. This embodiment is illustrated in FIG. 9, when die 350 is positioned downstream of the vacuum forming operation. The fibers must be blown from a die with such a force that they are able to extend in the capillaries of the macroscopically expanded, three-dimensional, apertured, plastic web. By varying the velocity of the meltblown fibers, the effective momentum and it turn the depth of penetration of the meltblown fibers into the capillaries of the plastic web can be varied. The fibers must be heated to such a temperature or the apertured, plastic web must be heated such that the meltblown fibers will adhere to the apertured, plastic web.

Figure 10:
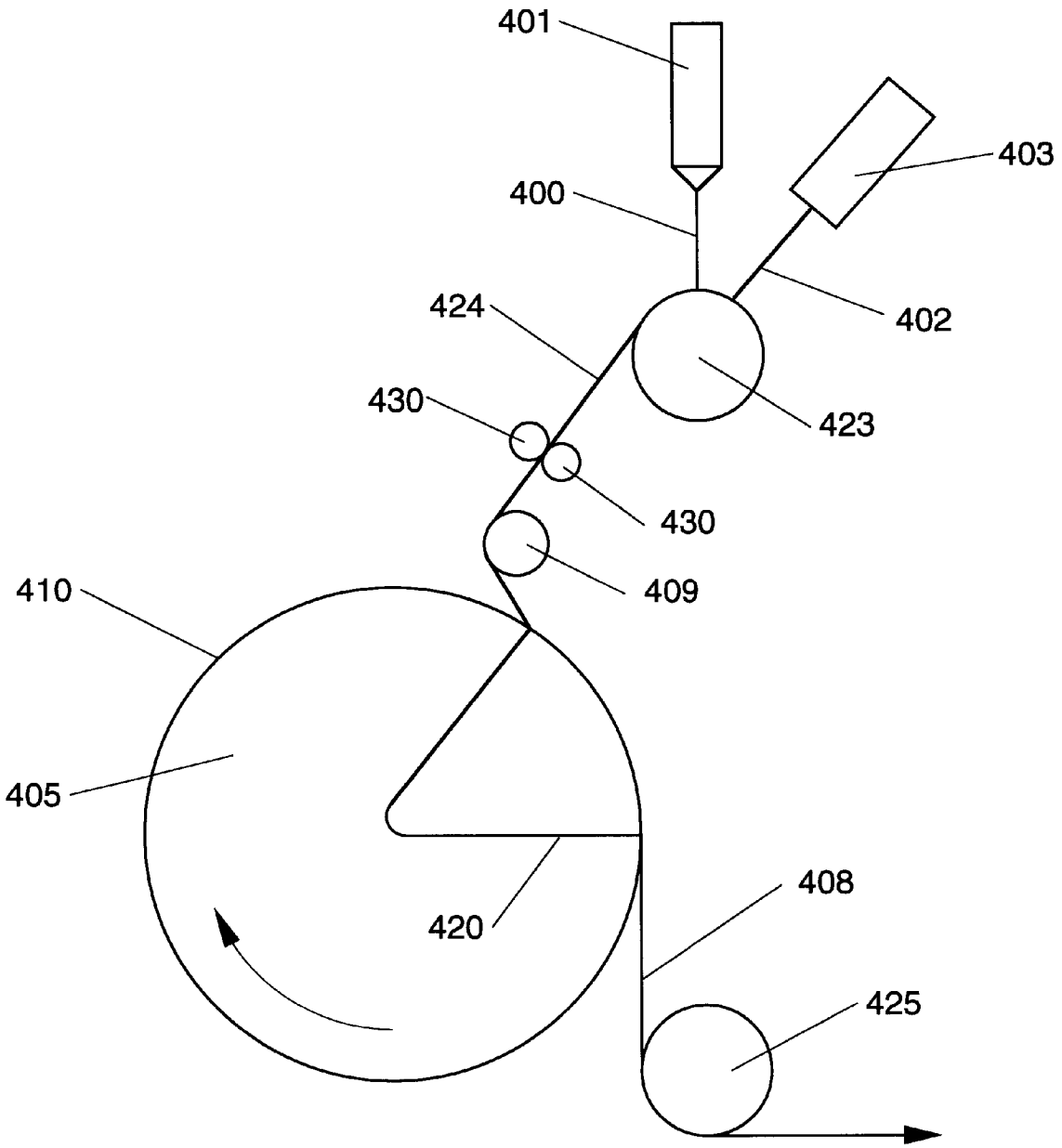
FIG. 10 is a simplified schematic representation of an alternative process for making the fibrous and apertured, plastic web of the present invention.

Another process for preparing the fibrous and apertured, plastic web of the present invention is shown in FIG. 10. A stream of meltblown fibers 402 is blown from die 403 onto the surface of drum 423. A web of molten resin 400 is extruded from a conventional extruder 401 onto meltblown fibers 402 to create a composite web 424. Composite web 424 is fed over nip roU 409 onto the surface of a forming drum 405 about which a forming structure 410 rotates such that the molten resin side of composite web 424 is in contact with forming structure 410. As the composite web 424 passes across internally located vacuum chamber 420 a pneumatic pressure is applied to composite web 424 to cause the composite web to be urged into substantial conformance with forming structure 410. Afer forming, web 408 is removed from forming drum 405 by way of nip roll 425.

In the process illustrated in FIG. 10, a set of calendaring rolls 430 may be added to help ensure that the composite web remains in tact. In the embodiment illustrated in FIG. 10, the calendaring rolls 430 are added prior to the composite web reaching the forming drum 405. Calendaring rolls may also be added after the formed web 408 is removed from forming drum 405.

The absorbent core 16 is positioned between the topsheet 12 and the backsheet 14. The absorbent core 16 may be any absorbent means which is capable of absorbing or retaining liquids (e.g., menses and/or urine). As shown in FIGS. 1–3, the absorbent core 16 has a body surface, a garment surface, side edges and end edges. The absorbent core 16 may be manufactured in a wide variety of sizes and shapes (e.g., rectangular, oval, hourglass, dog bone, asymmetric, etc.) and from a wide variety of lquid-absorbent materials commonly used in absorbent articles such as comnninuted wood pulp which is generally referred to as airfelt. Examples of other suitable materials include creped cellulose wadding, cross-linked cellulose fibers, absorbent foams, absorbent sponges, synthetic staple fibers, polymeric fibers, hydrogel-forming polymer gelling agents, peat moss, combinations of the foregoing, or any equivalent material or combinations of materials. The configuration and construction of the absorbent core may also be varied (e.g., the absorbent core may have varying caliber zones (e.g., profiled so as to be thicker in the center) hydrophilic gradients, super absorbent gradients, or lower density and lower average basis weight acquisition zones); or may comprise one or more layers or structures. The total absorbent capacity of the absorbent core should, however, be compatible with the desired loading and the intended use of the absorbent article. Further, the size and absorbent capacity of the absorbent core may be varied to accommodate different uses such as incontinence pads, pantiliners, regular sanitary napkins, or overnight sanitary napkins.

Suitable cross-linked cellulose fibers are described in U.S. Pat. No. 4,888,093, issued to Cook, et al. on Dec. 19, 1989; U.S. Pat. No. 4,822,543, issued to Dean, et al. on Apr. 18, 1989; U.S. Pat. No. 4,889,595, issued to Schoggen, et al. on Dec. 26, 1989; U.S. Pat. No. 4,889,596, issued to Schoggen, et al. on Dec. 26, 1989; U.S. Pat. No. 4,898,642 issued to Moore, et al. on Feb. 6, 1990; U.S. Pat. No. 4,935,022, issued to Lash, et al. on Jun. 19, 1990.

The characteristics of the absorbent core 16 for particular types of absorbent articles are described in greater detail in the patents and documents incorporated by reference herein, and the patents and other documents incorporated by reference in those documents, the disclosures of which are all incorporated by reference herein. Other suitable absorbent core arrangements are described in U.S. Pat. Nos. 4,988,344 and 4,988,345, and European Patent Application Publication No. 0 198 683, published Oct. 22, 1986 in the name of Duenk, et al. which are also incorporated by reference herein. The absorbent article could also include any additional layers or other components such as are described in the patents incorporated by reference. For example, the absorbent article 10 may comprise an acquisition layer or patch of cross-linked cellulose fibers positioned between the topsheet 12 and the absorbent core 16.

The backsheet 14 and the topsheet 12 are positioned adjacent to the garment surface and the body surface, respectively, of the absorbent core 16 and are preferably joined thereto and to each other by attachment means (not shown) such as those well known in the art. For example, the backsheet 14 and/or the topsheet 12 may be secured to the absorbent core 16 by a uniform continuous layer of adhesive, a patterned layer of adhesive, or an array of separate lines, spirals, spots of adhesive, or meltblown adhesives. Adhesives which have been found to be satisfactory are manufacture by HB Fuller Company of St. Paul, Minn. under the designation HL-1258. The attachment means will preferably comprise an open pattern network of filaments of adhesives as is disclosed in U.S. Pat. No. 4,573,986 issued to Minetola et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker et al. on Nov. 22, 1978; and U.S. Pat. No. 4,842,666 issued to Werenicz on Jun. 27, 1989. Each of the patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 14 is impervious to liquids and is preferably manufactured from a thin plastic film, although other flexible liquid impervious materials may also be used. The backsheet 14 prevents liquid contained in absorbent core 16 from wetting articles which contact the absorbent article 10. Polyethylene films having a thickness of from about 0.001 to about 0.002 inches (0.0025 to 0.0051 cm.) have been used for the backsheet 14 with satisfactory results. As used herein, the term "flexible" refers to materials which are compliant and which will readily conform to the general shape and contours of the human body.

The backsheet 14 is superimposed on the garment-facing side 16*b* of absorbent core 16 and preferably extends beyond the edges thereof. The topsheet 12 is superimposed over the body-facing side 16*a* of the absorbent core 16, and may also extend beyond the edges of the core 16. The absorbent core 16 is, therefore, positioned between the topsheet 12 and the backsheet 14. The topsheet 12 and backsheet 14 are joined to each other such as around their peripheries. The topsheet 12 and backsheet 14 can be joined in any suitable manner such as by the use of adhesives, crimping, heat-sealing, or ultrasonic bonding.

While a number of particularly preferred embodiments in the present invention have been illustrated and described, it will be obvious to those skilled in the art that various changes and modifications can be made without the departing from the spirit and scope of the invention, and it is intended to the appended claims all such modifications that are in the scope of this invention.

What is claimed:

1. A process for forming a fibrous and apertured, three-dimensional, macroscopically expanded web having a fibrous wearer-contacting surface, said process comprising the steps of:

(a) extruding a polymeric resin onto a forming structure to form a semi-molten film web, said forming structure exhibiting a macroscopic, three-dimensional, cross-section defined by a multiplicity of macroscopic apertures which place opposed surfaces of said forming structure in fluid communication with one another;

(b) providing a web of nonwoven fabric;

(c) disposing said web of nonwoven fabric onto said semi-molten film web while said semi-molten film web is supported by said forming structure so as to join said webs to form a composite web; and (d) applying a pneumatic pressure to said composite web to cause said composite web to be urged into substantial conformance with the macroscopic, three-dimensional, cross-section of said forming structure forming a three-dimensional, macroscopically expanded, formed web having first and second surfaces. said formed web having a plurality of capillaries extending from said first surface to said second surface, said capillaries being defined by a plurality of sidewall portions interconnected to one another intermediate said first and second surfaces and terminating in said second surface, said pneumatic pressure causing said fibers to be pulled against said first surface of said formed web and into said capillaries of said formed web along said sidewall portions, said fibers being secured to said first surface and said sidewall portions of said formed web such that said capillaries are substantially free of fibers spanning across said capillaries between opposing sidewall portions forming said fibrous wearer-contacting surface of said fibrous and apertured, three-dimensional, macroscopically expanded web.

* * * * *